United States Patent
Albus (10) Patent No.: US 9,233,252 B2
(45) Date of Patent: Jan. 12, 2016

(54) HANDHELD DEVICE FOR A PATIENT

(75) Inventor: Marco Albus, Berlin (DE)

(73) Assignee: Biotronik CRM Patent AG (CH)

( * ) Notice: Subject to any disclaimer, the term of this patent is extended or adjusted under 35 U.S.C. 154(b) by 1887 days.

(21) Appl. No.: 12/427,781

(22) Filed: Apr. 22, 2009

(65) Prior Publication Data

US 2009/0284486 A1 Nov. 19, 2009

(30) Foreign Application Priority Data

May 13, 2008 (DE) .......................... 10 2008 023 328

(51) Int. Cl.
| | |
|---|---|
| *G06F 3/041* | (2006.01) |
| *A61N 1/372* | (2006.01) |
| *A61B 5/00* | (2006.01) |
| *G06F 19/00* | (2011.01) |
| *G08C 17/00* | (2006.01) |
| *A61N 1/05* | (2006.01) |
| *A61N 1/36* | (2006.01) |

(52) U.S. Cl.
CPC ............ *A61N 1/37247* (2013.01); *A61B 5/743* (2013.01); *A61B 5/7435* (2013.01); *A61B 5/7475* (2013.01); *G06F 19/3406* (2013.01); *G06F 19/3412* (2013.01); *G08C 17/00* (2013.01); *A61N 1/0551* (2013.01); *A61N 1/36071* (2013.01)

(58) Field of Classification Search
None
See application file for complete search history.

(56) References Cited

U.S. PATENT DOCUMENTS

| | | | |
|---|---|---|---|
| 5,771,001 A * | 6/1998 | Cobb ......................... | 340/573.1 |
| 6,198,394 B1 * | 3/2001 | Jacobsen et al. ........... | 340/573.1 |
| 7,248,159 B2 * | 7/2007 | Smith ....................... | 340/539.13 |
| 7,285,090 B2 * | 10/2007 | Stivoric et al. ................ | 600/300 |
| 7,629,881 B2 * | 12/2009 | Gao et al. ................. | 340/539.13 |
| 7,753,845 B2 * | 7/2010 | Gopinathan et al. .......... | 600/300 |
| 2002/0030682 A1 | 3/2002 | Eberlein | |
| 2002/0116036 A1 | 8/2002 | Daignault, Jr. et al. | |
| 2005/0015115 A1 | 1/2005 | Sullivan et al. | |
| 2005/0192972 A1 | 9/2005 | Daignault, Jr. et al. | |
| 2007/0276195 A1 | 11/2007 | Xu et al. | |
| 2008/0297527 A1 | 12/2008 | Daignault, Jr. | |

FOREIGN PATENT DOCUMENTS

| | | | |
|---|---|---|---|
| WO | WO 0193952 A1 | 12/2001 | |
| WO | WO 2004041080 A2 | 5/2004 | |
| WO | WO 2005009536 A1 | 2/2005 | |
| WO | WO 2007133556 A2 | 11/2007 | |

* cited by examiner

*Primary Examiner* — K. Wong (74) *Attorney, Agent, or Firm* — Craig A. Fieschko, Esq.; DeWitt Ross & Stevens S.C.

(57) ABSTRACT

A handheld device (10) has a graphic display (12), an interface (18) for wireless data transmission, an input unit (14) for input of control commands, and a control unit (16) connected to the display (12), the interface (18), and the input unit (14). The control unit (16) is designed to display a schematic diagram of a human body on the graphic display (12) and to allow a selection of partial regions of the diagram with the help of the input unit (14).

20 Claims, 6 Drawing Sheets

HANDHELD DEVICE FOR A PATIENT

FIELD OF THE INVENTION

The invention relates to a handheld device having a graphic display; an interface for wireless data transmission; an input unit for input of control commands; and a control unit connected to the display, the interface, and the input unit. The invention relates in particular to such a handheld device for use by a patient, and the purpose of such a handheld device is to support medical observation of a patient, or treatment of a patient.

BACKGROUND OF THE INVENTION

The object of the invention presented here is to create a device which supports the treatment of a patient and thereby improves such treatment.

SUMMARY OF THE INVENTION

According to this invention, this object is achieved by a handheld device of the aforementioned type in which the control unit is designed to display a schematic diagram of a human body on the graphic display, and to allow a selection of one or more partial regions of the display with the help of an input unit.

In this way, the handheld device offers an intuitive interface for the patient which makes it possible for the patient to easily select parts of the displayed diagram of the body by selecting a corresponding partial region of the diagram of the body, and by being able to, for example, mark areas of the body where the patient has observed or felt something unusual, e.g., feeling pain or seeing reddening of the skin. An especially preferred area for use of such a handheld device is in pain therapy.

The control unit is preferably designed to control the display in such a way that outlines for selectable partial regions of the body are discernible in the diagram of the human body. This makes it easier for a patient to mark certain partial regions in a targeted manner, and also allows easier operation of the handheld device where a touch-sensitive graphic display (touch screen) is used for input, as well as where a touchpad or key control is used as the input unit.

The control unit is preferably designed to trigger the display in response to selection of a partial region of a diagram of the body, such that one or more partial regions selected in this way are displayed differently graphically than the partial regions not selected. In this way the patient receives immediate feedback in response to his input and knows exactly which choice was received by the handheld device.

In an especially preferred version of the handheld device, the control unit is designed to input the entry of a value to be assigned to a partial region in response to selection of said partial region of the diagram of the body, e.g., a value representing the intensity of pain or representing the reddening of an area of skin. The value may be only divalent, e.g., weak or strong, or trivalent, and the value may be characterized by appropriate symbols or by display of touch-sensitive fields on the graphic display for each available value. In the latter case, the patient need only select one of several value fields on the graphic display after selecting a partial region of the diagram of the body in order to assign a valuation, e.g., "slight pain" or "very severe pain" to the previously selected partial region of the diagram of the body.

In another preferred version of the invention, the handheld device has a memory connected to a control unit such that the control unit is designed to assign a selection of one or more partial regions to the diagram of the body and optionally also assign a current date to each respective value to be assigned, and to store the identifier of the selected partial region and optionally the assigned value together with the current date in the memory. In this way, a type of diary of the course of the disease can be displayed easily. In this context, it is especially advantageous if the handheld device is also designed to instruct the patient at regular intervals, e.g., daily, to make a selection of possible body areas affected by disease and to make an assignment of a corresponding value.

In addition, in a preferred version of the handheld device, the control unit is designed to display parameters for treatment and the respective value fields on the graphic display. The control unit can also receive values for the respective treatment parameters via the input unit, display them on the graphic display, and store the respective input value in the memory correlated with the respective treatment parameter. The treatment may be, for example, pain therapy by means of a stimulation device. The therapy parameters would then be the parameters that define the incidence, for example, of therapeutic electric pulses and their electric properties such as frequency, amplitude or pulse width.

The handheld device here may even be designed to automatically form suitable values for the treatment parameters, with the values being formed on the basis of information from a patient pertaining to the selection of partial regions from the diagram of the body that might be affected by pain, as well as the intensity of the pain perceived at these regions.

Thus corresponding values for the treatment parameters can be entered manually by a patient or, better yet, by a physician, or can be generated automatically by the handheld device.

In addition, the handheld device is preferably designed to process values formed automatically or entered manually for a respective treatment parameter in such a way as to yield program parameters for a stimulation device. The control unit is also designed to transmit these program parameters over the interface for wireless data transmission, e.g., to a stimulation device.

In addition, it is preferable if the handheld device is designed to display not just a single schematic diagram of a human body on the graphic display, but instead to show several schematic diagrams of the human body from various views, e.g., from a front view and a rear view.

Additional preferred versions of the invention are derived by combining the preferred features listed above, as well as from the following description of a preferred exemplary version.

BRIEF DESCRIPTION OF THE DRAWINGS

The invention will now be explained in greater detail with reference to an exemplary version shown in the figures. The figures show.

Figure 1:
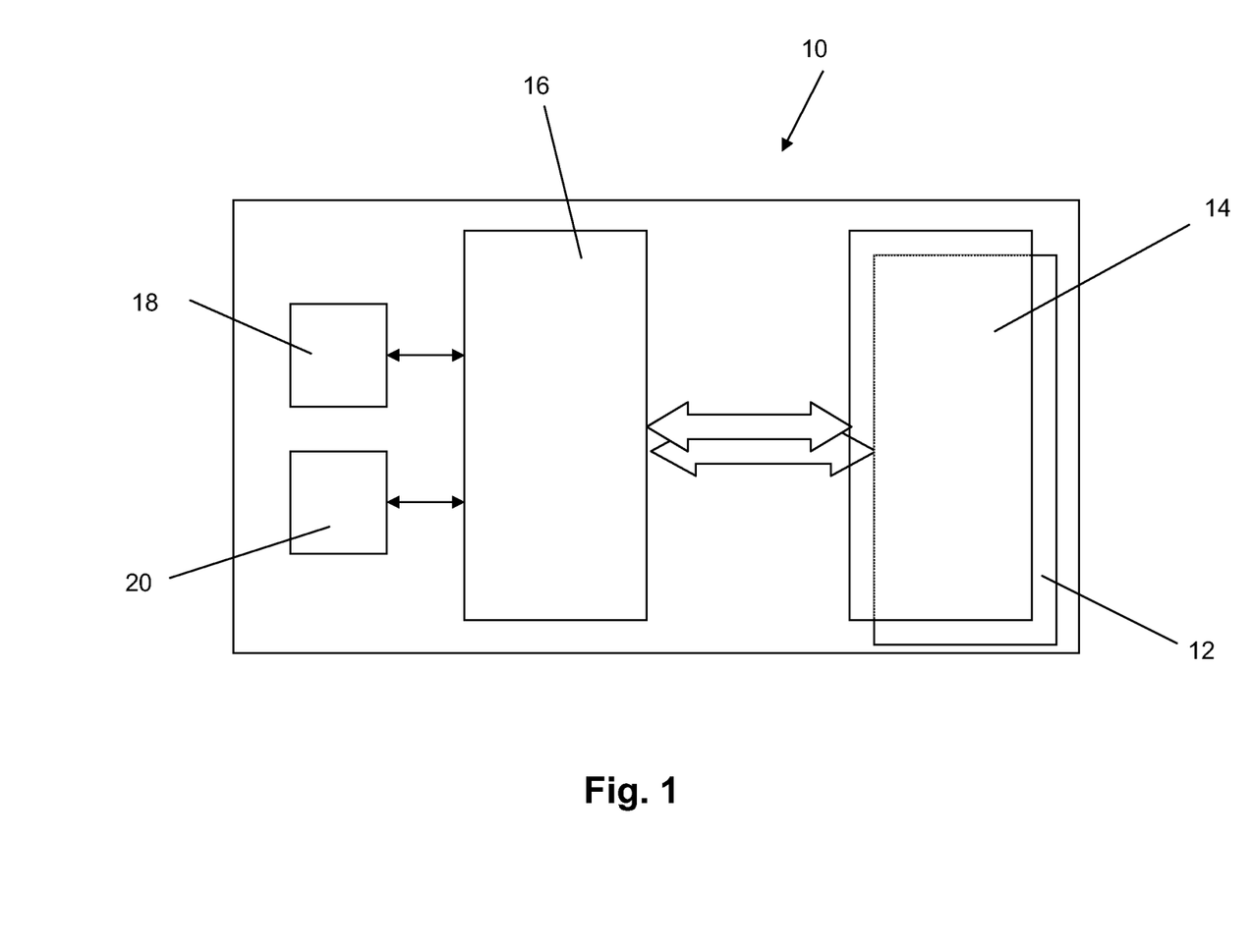
FIG. 1: a schematic block diagram of the exemplary handheld device.

FIG. 1 shows a schematic block diagram of the inventive handheld device 10. Preferred components include a graphic display 12 and an input device 14, which are preferably provided in the form of a touch-sensitive display screen designed in a known manner to detect touch and the location of the respective touch. As a touch-sensitive display screen (touch screen), the graphic display 12 is thus also an input unit 14 of the handheld device 10 at the same time. In an essentially known manner, touching of the graphic display 12 in certain partial regions results in this touch being interpreted as an input. The graphic display and the input unit are connected to a control unit 16, which in particular also controls which type of input will be assigned to a detected touching of the touch screen at a particular location. Furthermore, an interface 18 for wireless data transmission and a memory 20 are connected to the control unit 16.

Figure 2A:
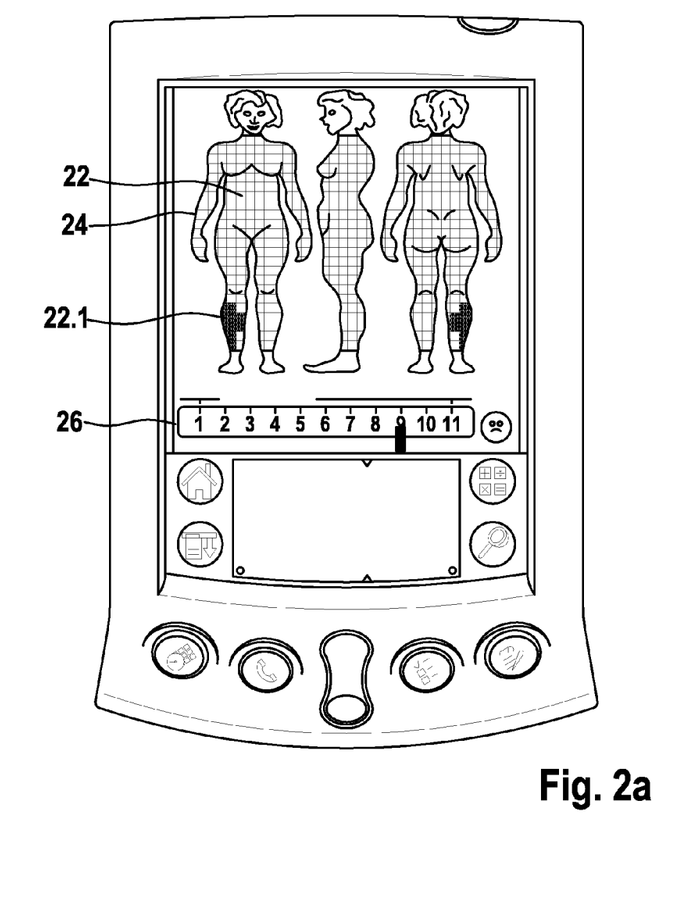
FIGS. 2a and 2b: two diagrams of an exemplary handheld device with a diagram of the body on a graphic display.
Figure 2B:
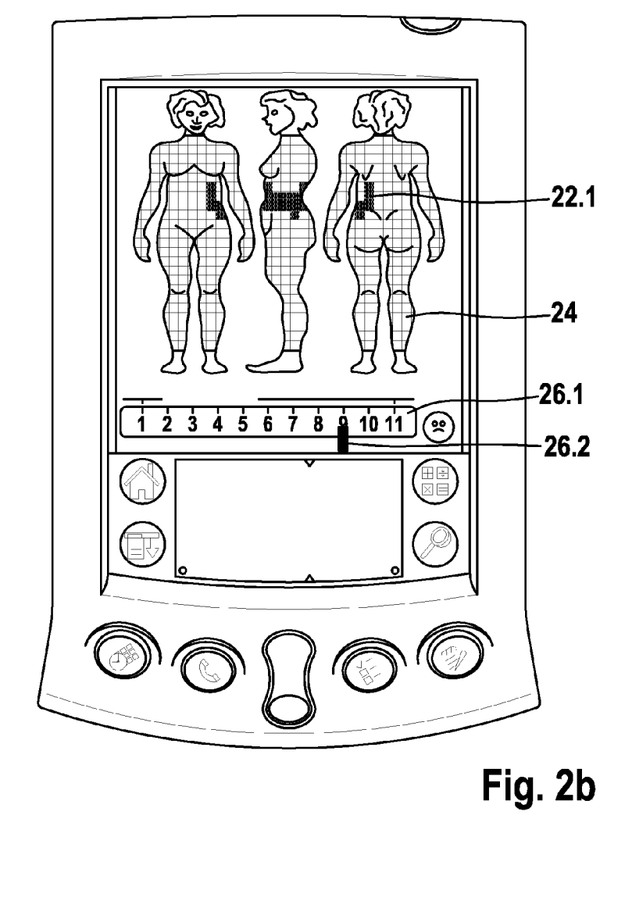

FIG. 2 shows the inventive handheld device 10 in a first operating mode, which allows a patient to indicate in a simple manner which areas of the body are causing him pain and also to indicate the intensity of the pain perceived by the patient.

To do so, the control unit 16 of the handheld device 10 and thus the handheld device 10 itself are designed so that the graphic display 12 displays three different diagrams 24 of a body that has been subdivided into partial regions 22 and consists of a front view, a side view and a rear view. The handheld device 10 is designed so that selection (touching) of a respective partial region 22 of a respective body diagram 24 indicates an input, and the control unit 16 will receive the input for the selected partial region 22. FIGS. 2a and 2b each illustrate exemplary versions in which different partial regions 22.1 of the respective body diagrams 24 are selected.

The control unit 16 of the handheld device 10 is also designed so that a value, e.g., a pain value, can be assigned to a particular selected partial region 22.1 of the respective body diagram 24.

For this purpose, the control unit is also designed to allow the display of an input field 26 for such a pain value to be assigned to a selected partial region 22.1 on the graphic display 12. In this exemplary version, this display field 26 is embodied in the form of a scale 26.1, to which an indicator 26.2 is assigned, with the indicator being displaceable by touch operation, to thereby adjust a pain level which is to be assigned to a particular selected partial region of the body diagram.

As also shown by FIGS. 2a and 2b, selected partial regions 22.1 of the body diagram 24 are emphasized in color in the body diagram 24 in order to display to the patient which body region(s) he has selected.

The scale 26.1 of the display field 26 is also shown in color, where the colors are selected like a rainbow with a fluid transition from one to the other. The left end of the scale 26.1 is shown in blue accordingly, developing into green and yellow and then a red color at the right end of the scale 26.1. Blue or green segments of the scale 26.1 represent lower pain values, whereas yellow or orange or red segments of the color scale represent higher pain values.

If the patient assigns a pain value to a partial region 22.1 of the body diagram 24 selected previously by displacement of the pointer 26.2, the partial region 22.1 of the body diagram 24 thereby selected is preferably shown in the color from the scale 26.1 for the particular pain value thereby selected.

On the whole, this yields an interface of the handheld device 10 that can be used intuitively by the patient to easily input information about his pain perception.

The information input by the patient is provided with a time stamp containing information about the date and time of day by the control unit 16, and is stored in a memory 20 of the handheld device 10.

Figure 3:
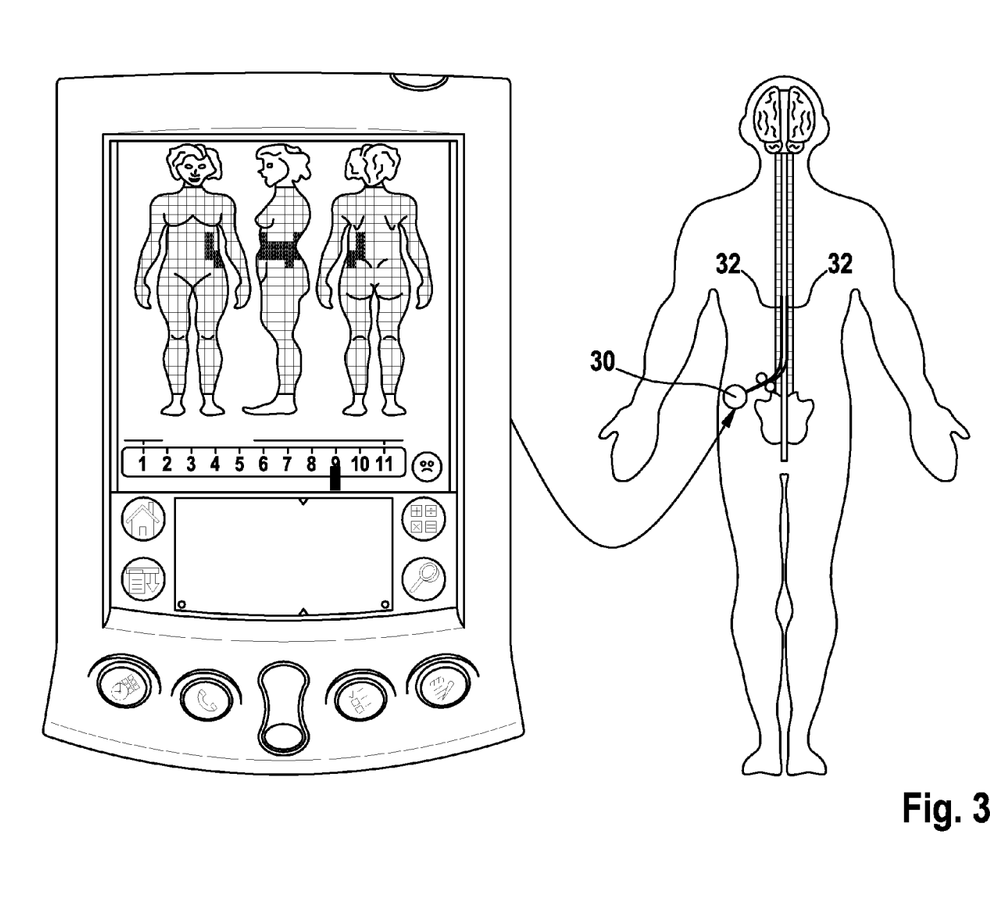
FIG. 3: a handheld device like that from FIG. 2 connected to an implant for pain therapy.

As shown in FIG. 3, the handheld device 10 is preferably also designed to control an implant 30 for pain therapy. The implant 30 is connected to electrodes 32 for spinal stimulation of a patient and is designed to deliver electric pulses to the patient's spine via the electrodes 32. The frequency, pulse width, amplitude and other characteristics of the stimulation pulses to be delivered are adjustable here (see also FIG. 4).

Figure 4:
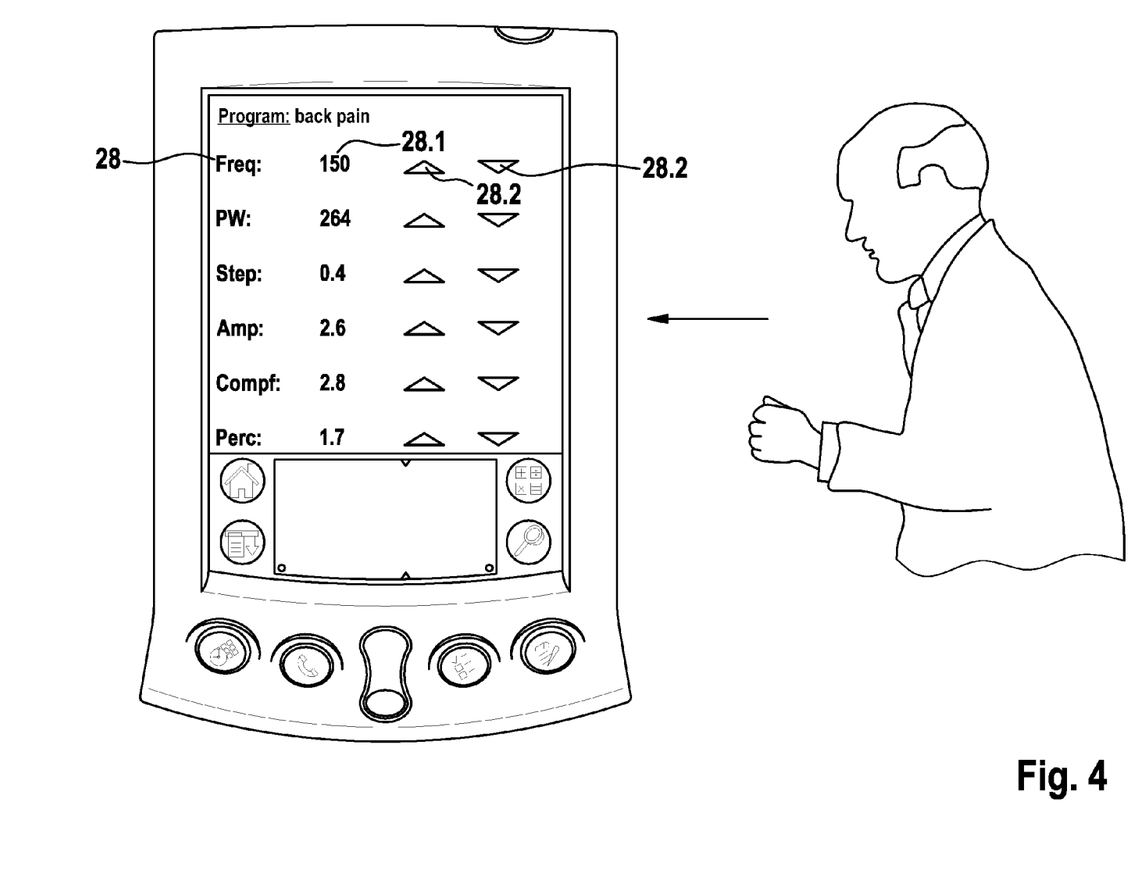
FIG. 4: the handheld device from the preceding figures with a display for input and storage of values for treatment parameters.

FIG. 4 shows the handheld device 10 in an operating mode in which the control unit 16 causes the graphic display 12 to display treatment parameters 28 and also values 28.1 and touchpads 28.2 assigned to the particular treatment parameter so that the particular value assigned to a treatment parameter is to be displayed. Touchpads 28.2 are input elements which, when touched, result in a change in the particular assigned value of the treatment parameter. As shown in FIG. 4, the touchpads 28.2 may be in the form of arrow diagrams, so that touching the particular up arrow at the left results in an increase in the respective value of the treatment parameter and touching the respective right touchpad with the down arrow results in a reduction in the particular value of the treatment parameter. As an example, FIG. 4 shows individual treatment parameters for adjusting electric pulses for pain therapy, namely (from top to bottom) the frequency, the pulse width and the stimulation amplitude.

The displayed values 28.1 of the treatment parameters may be reasonable starting values programmed into the handheld device 10.

However, the displayed values may also be calculated automatically by the control unit 16 of the handheld device 10 on the basis of the inputs received previously for selection of partial regions of the body diagram and the respective pain values. In the latter case, the operating mode of the handheld device 10 illustrated in FIG. 4 serves to manually correct the automatically determined values for the treatment parameters.

Figure 5:
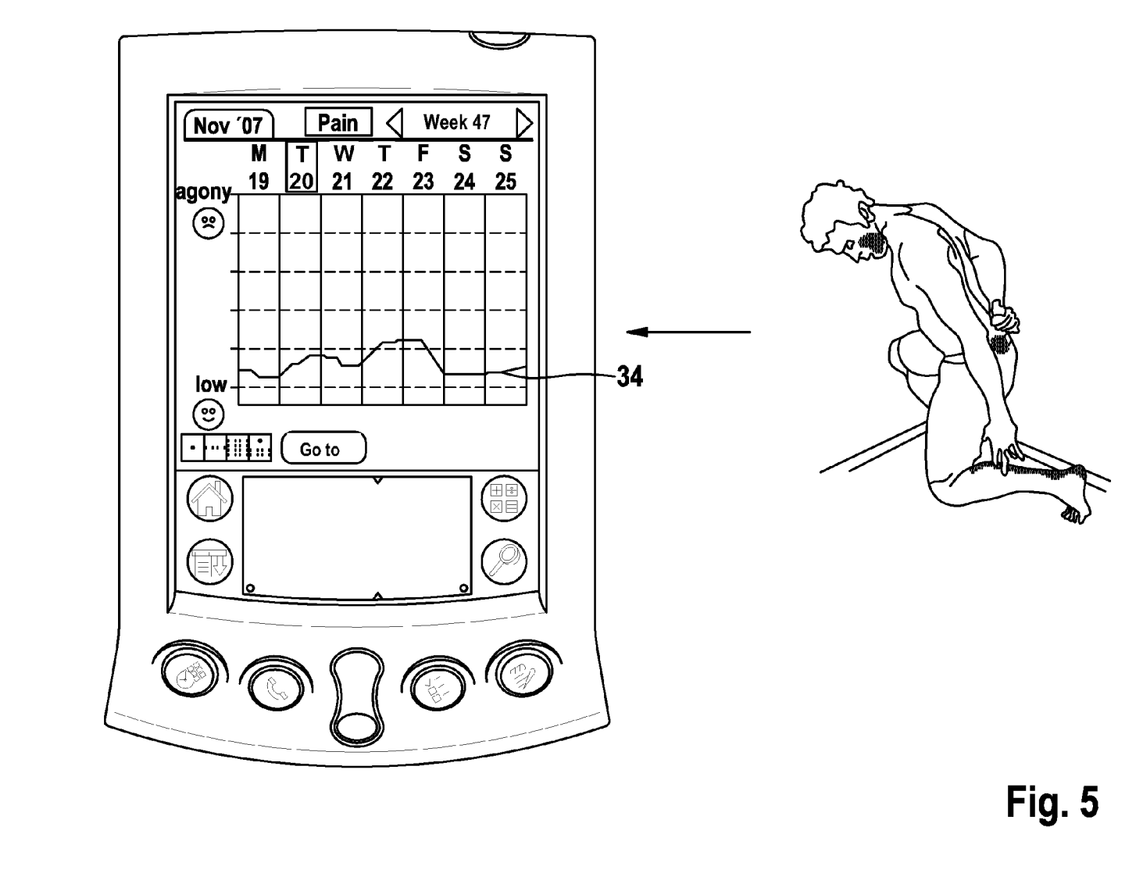
FIG. 5: the handheld device from the preceding figures with a graphic display of previously input values.

Finally, FIG. 5 shows how a diagram 34 can be derived from the patient's input for selection of particular partial regions of the body diagram affected by pain and the particular assigned intensity of the pain in the form of a value, this diagram 34 having been calculated by the control unit and displayed on the graphic display screen 12. The diagram 34 shown in FIG. 5 is generated from stored values by the computer unit and illustrates the course of pain values over several days.

Figure 6:
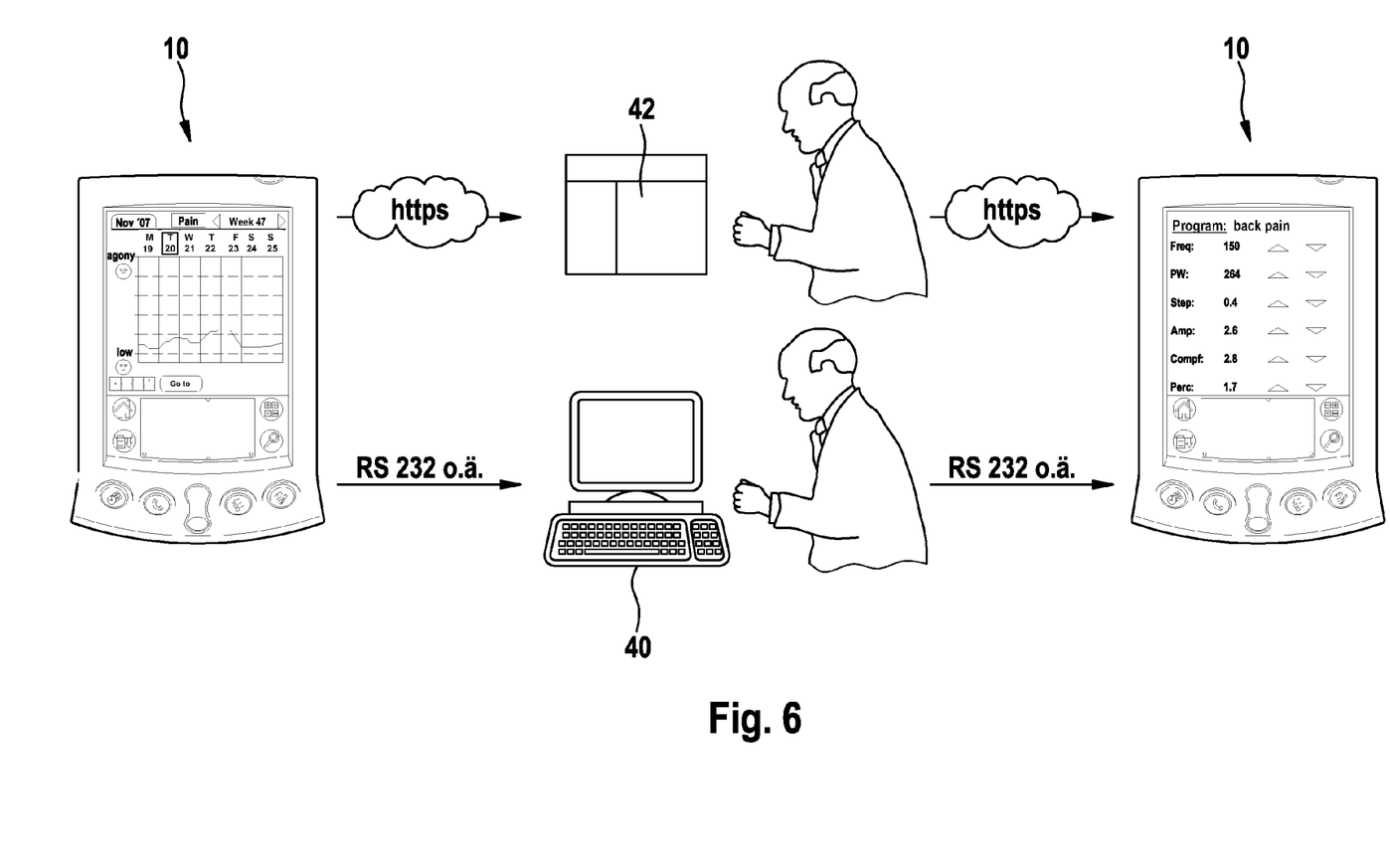
FIG. 6: a diagram illustrating the readout and transfer of data from one handheld device to the other.

FIG. 6 illustrates how a handheld device 10 can transmit a diagram such as diagram 34 over the Internet via the interface 18 or another interface, so that the diagram can be assessed by a physician. In addition, FIG. 6 shows in the top row that the physician can adjust the treatment parameters for the handheld device 10 after assessing the diagram and can again transmit them over the Internet to the treatment device 10.

The bottom row in FIG. 6 illustrates that the handheld device 10 may also be connected by a wired interface to a computer 40 situated in the immediate vicinity of the handheld device 10, so that a diagram 34 can be transmitted to the computer 40 in a manner similar to that indicated in the top row of FIG. 6. On the computer 40, a physician can create suitable values for the treatment parameters and can in turn transmit them over a wired interface to the handheld device 10.

As FIG. 6 shows, diary entries and treatments retrieved can be read out of the handheld device 10. Again, this data can either be entered manually into another data processing system 40 or retrieved remotely via the telematic connection 42.

In addition, the physician may store or modify program settings in the mobile device by way of a secure interface so the patient can then retrieve this new adjusted treatment.

What is claimed is:

1. A handheld device (10) including:
   a. a graphic display (12),
   b. an input unit (14) for entering control commands,
   c. an interface (18) for wireless data transmission, and
   d. a control unit (16) in communication with the graphic display (12), the interface (18), and the input unit (14), wherein the control unit (16):
      (1) controls the display of a schematic diagram of a human body on the graphic display (12), and
      (2) collects input from the input unit (14) corresponding to the selection of one or more partial regions of the schematic diagram.

2. The handheld device (10) of claim 1 wherein the graphic display (12) shows the schematic diagram of the human body with borders being shown for each of the selectable partial regions of the diagram.

3. The handheld device (10) of claim 2 wherein the graphic display (12), upon selection of a partial region of the schematic diagram by a corresponding input from the input unit, alters the appearance of the selected partial region to appear differently from partial regions of the schematic diagram which have not been selected.

4. The handheld device (10) of claim 2 wherein the graphic display (12), upon selection of a partial region of the schematic diagram by a corresponding input from the input unit, alters the appearance of the selected partial region within the borders of the selected partial region.

5. The handheld device (10) of claim 1 wherein the graphic display (12) shows two or more schematic diagrams of the human body, each diagram showing the human body from a different perspective.

6. The handheld device (10) of claim 5 wherein:
   a. each schematic diagram of the human body is shown with borders for each of the selectable partial regions of the diagram, and
   b. at least some of the selectable partial regions are shown in two or more of the schematic diagrams, and
   c. the graphic display (12), upon selection of a partial region by a corresponding input from the input unit on any one of the schematic diagrams, alters the appearance of the selected partial region in all of the schematic diagrams wherein the selected partial region is depicted, such that the selected partial region appears differently from partial regions which have not been selected.

7. The handheld device (10) of claim 1 wherein, upon the selection of a partial region of the schematic diagram, the control unit (16) further collects input from the input unit (14) corresponding to a value to be assigned to the selected partial region.

8. The handheld device (10) of claim 1 further including a memory in communication with the control unit, wherein upon selection of a partial region by a corresponding input from the input unit, the memory stores:
   a. the time of the input, and
   b. the identity of the partial region.

9. The handheld device (10) of claim 8 wherein, upon the selection of a partial region of the diagram:
   a. the control unit (16) further collects input from the input unit (14) corresponding to a value to be assigned to the selected partial region, and
   b. the memory stores the time of the input and the input value.

10. The handheld device (10) of claim 1:
    a. wherein the graphic display (12) shows:
       (1) parameters (28) for pain therapy, and
       (2) corresponding values (28.1) for the parameters,
    b. wherein the input unit (14) collects input determining the value (28.1) of one or more of the parameters, and
    c. further including a memory in communication with the control unit, wherein the memory stores the values (28.1) of the one or more parameters.

11. The handheld device (10) of claim 10 wherein the input values of the one or more parameters are wirelessly transmitted via the interface (18) for wireless data transmission.

12. The handheld device (10) of claim 10 wherein the control unit (16) generates control instructions for a stimulation device (30), the control instructions being at least partially derived from the stored input values of the one or more parameters.

13. The handheld device (10) of claim 1 wherein the control unit (16), upon receipt of an inquiry command from the interface (18) for wireless data transmission, transmits:
    a. the identity of the selected partial regions, and
    b. the time of the selection of the one or more partial regions of the diagram.

14. The handheld device (10) of claim 1:
    a. wherein the graphic display (12) shows:
       (1) parameters (28) for pain therapy, and
       (2) corresponding values (28.1) for the parameters,
    b. wherein the values (28.1) for the parameters are set by the control unit (16) at least in part from input received wirelessly by the interface (18) for wireless data transmission.

15. A handheld device (10) including:
    a. a graphic display (12),
    b. an input unit (14) for entering control commands, the input unit (14) being at least partially coincident with the graphic display (12);
    c. a control unit (16) in communication with the graphic display (12) and the input unit (14), wherein the control unit (16):
       (1) controls the display of a schematic diagram of a human body on the graphic display (12), the schematic diagram showing the body partitioned into distinct partial regions;
       (2) collects input from the input unit (14) corresponding to:
          (a) the selection of one or more of the partial regions of the schematic diagrams, and
          (b) a value to be assigned to each of the selected partial regions.

16. The handheld device (10) of claim 15 in combination with a stimulation device (30), wherein the control unit (16) generates control instructions for the stimulation device (30), the control instructions being at least partially dependent on the values assigned to the partial regions.

17. The handheld device (10) of claim 16 further including an interface (18) for wireless data transmission, wherein the interface (18) transmits the control instructions to the stimulation device (30).

18. The handheld device (10) of claim 15 further including an interface (18) for wireless data transmission, wherein the interface (18):
    a. transmits the collected values to be assigned to each of the selected partial regions, and b. receives control instructions for a stimulation device (30), the control instructions being at least partially derived from the transmitted values.

19. The handheld device (10) of claim 15 wherein:
   a. the graphic display (12) shows two or more schematic diagrams of the human body, each diagram:
      (1) showing the human body from a different perspective, and
      (2) showing the body partitioned into distinct partial regions;
   b. the control unit (16), upon collecting input from the input unit (14) corresponding to the selection of one of the partial regions, alters the appearance of the selected partial region in all of the schematic diagrams wherein the selected partial region is depicted, such that the selected partial region appears differently from partial regions which have not been selected.

20. A handheld device (10) including:
   a. a graphic display (12), the graphic display:
      (1) incorporating an input unit (14) for entering control commands, and
      (2) showing a schematic diagram of the human body partitioned into distinct partial regions;
      wherein an input can be entered at any of the partial regions to indicate selection of the partial region;
   b. a control unit (16) in communication with the graphic display (12) and the input unit (14), wherein the control unit (16) collects input from the input unit (14) corresponding to:
      (1) the selection of one or more of the partial regions of the schematic diagrams, and
      (2) a value to be assigned to each of the selected partial regions;
   c. an interface (18) in communication with the control unit (16), wherein the interface (18) transmits:
      (1) data corresponding to the values assigned to the selected partial regions, and
      (2) data corresponding to control instructions for a stimulation device (30), the control instructions being at least partially derived from the values assigned to the selected partial regions.

* * * * *